US011266386B2

(12) United States Patent
Ago et al.

(10) Patent No.: US 11,266,386 B2
(45) Date of Patent: Mar. 8, 2022

(54) ADAPTER, ROBOTIC SURGICAL SYSTEM, AND ADAPTER ATTACHING METHOD

(71) Applicant: Medicaroid Corporation, Kobe (JP)

(72) Inventors: Kenji Ago, Kobe (JP); Yu Usuki, Kobe (JP); Shota Betsugi, Kobe (JP); Yoshiaki Tanaka, Kobe (JP); Tetsuya Nakanishi, Kobe (JP)

(73) Assignee: MEDICARDOID CORPORATION, Kobe (JP)

( * ) Notice: Subject to any disclaimer, the term of this patent is extended or adjusted under 35 U.S.C. 154(b) by 176 days.

(21) Appl. No.: 16/825,428

(22) Filed: Mar. 20, 2020

(65) Prior Publication Data

US 2020/0305852 A1 Oct. 1, 2020

(30) Foreign Application Priority Data

Mar. 28, 2019 (JP) .............................. JP2019-063443

(51) Int. Cl.
*A61B 17/00* (2006.01)
*A61B 34/37* (2016.01)
(Continued)

(52) U.S. Cl.
CPC .............. *A61B 17/00* (2013.01); *A61B 34/37* (2016.02); *A61B 46/10* (2016.02);
(Continued)

(58) Field of Classification Search
CPC ........................................... A61B 2017/00477
See application file for complete search history.

(56) References Cited

U.S. PATENT DOCUMENTS

| 8,142,447 B2 | 3/2012 | Cooper et al. |
| 2002/0032451 A1 | 3/2002 | Tierney et al. |
| 2014/0305995 A1* | 10/2014 | Shelton, IV ......... A61B 17/072 227/180.1 |

(Continued)

FOREIGN PATENT DOCUMENTS

| CN | 106361433 B | 11/2018 |
| EP | 3 232 973 A1 | 10/2017 |

(Continued)

OTHER PUBLICATIONS

Office Action (Notice of Reasons for Refusal) dated Jan. 19, 2021, by the Japanese Patent Office in corresponding Japanese Patent Application No. 2019-063443 and an English Translation of the Office Action. (6 pages).

(Continued)

*Primary Examiner* — Scott Luan
(74) *Attorney, Agent, or Firm* — Buchanan Ingersoll & Rooney PC

(57) ABSTRACT

The adapter includes: a base body that includes a first surface attached to a robot arm, and a second surface to which a surgical instrument is attached; an engaging portion that engages with the robot arm at an advanced position corresponding to an opening of the first surface; an urging member that urges the engaging portion in a direction from a retracted position to the advanced position; an operation portion connected to the engaging portion to shift the engaging portion to the retracted position while resisting an urging force of the urging member; and a stopper that stops the operation portion to prevent a shift of the engaging portion from the retracted position to the advanced position.

20 Claims, 11 Drawing Sheets

(51) Int. Cl.
  *A61B 46/10*   (2016.01)
  *A61B 34/30*   (2016.01)

(52) U.S. Cl.
  CPC ............... *A61B 2017/00115* (2013.01); *A61B 2017/00486* (2013.01); *A61B 2017/00973* (2013.01); *A61B 2034/301* (2016.02)

(56) References Cited

U.S. PATENT DOCUMENTS

| | | |
|---|---|---|
| 2017/0086930 A1 | 3/2017 | Thompson et al. |
| 2018/0000472 A1 | 1/2018 | Beira |
| 2019/0038283 A1 | 2/2019 | Shelton, IV et al. |
| 2019/0192241 A1 | 6/2019 | Xu et al. |
| 2019/0239966 A1 | 8/2019 | Xu et al. |

FOREIGN PATENT DOCUMENTS

| | | |
|---|---|---|
| JP | 2017-513552 A | 6/2017 |
| WO | 2011/143024 A1 | 11/2011 |
| WO | 2016/097861 A1 | 6/2016 |
| WO | 2018/041204 A1 | 3/2018 |

OTHER PUBLICATIONS

Cryptic Woodworks: "Spring Open Drawer Box", (Jun. 27, 2020), Retrieved from the Internet: URL:https://www.youtube.com/watch?v=4GHjl6W6s6M [retrived on Aug. 7, 2020], (1 page) XP054980758.
The extended European Search Report dated Aug. 18, 2020, by the European Patent Office in corresponding European Patent Application No. 20163696.6-1115. (13 pages).

\* cited by examiner

ADAPTER, ROBOTIC SURGICAL SYSTEM, AND ADAPTER ATTACHING METHOD

CROSS-REFERENCE TO RELATED APPLICATIONS

This application claims priority to Japanese Patent Application No. 2019-063443 filed on Mar. 28, 2019, the entire content of which is incorporated herein by reference.

BACKGROUND ART

The present disclosure relates to an adapter, a robotic surgical system, and an adapter attaching method, and particularly to an adapter for detachably connecting a surgical instrument to a robot arm of a robotic surgical system, a robotic surgical system including the adapter, and an adapter attaching method.

An adapter for detachably connecting a surgical instrument to a robot arm of a robotic surgical system is known (see, for example, U.S. Pat. No. 8,142,447).

U.S. Pat. No. 8,142,447 discloses an adapter including a latch for detachably attaching to an attachment portion of a robot arm, and an input unit for transmitting a driving force of the robot arm to the surgical instrument. According to the adapter disclosed in U.S. Pat. No. 8,142,447, the latch is bent and hooked on the attachment portion of the robot arm to fix the adapter to the robot arm.

SUMMARY

However, according to the adapter in U.S. Pat. No. 8,142,447, which uses the latch bent and hooked on the attachment portion of the robot arm to fix the adapter to the robot arm, there needs to engage the adapter to with the robot arm while applying a force for bending and deforming the latch when the adapter is attached to (engaged with) the robot arm. This configuration therefore produces a problem that easy attachment and detachment of the adapter to and from the robot arm is difficult.

An object of the present disclosure is to easily attach and detach an adapter to and from a robot arm of a robotic surgical system in which a surgical instrument is detachably connected to the robot arm using the adapter.

An adapter according to a first aspect of the present disclosure is detachably provided on a robot arm, and transmits a driving force from the robot arm to a surgical instrument. The adapter includes a base body, an engaging portion, an urging member, an operation member, and a stopper. The base body includes a first surface including an opening and attached to the robot arm, and a second surface to which the surgical instrument is attached. The engaging portion is configured to be movable between an advanced position corresponding to the opening of the first surface and a retracted position retracted from the advanced position, and engages with the robot arm at the advanced position. The urging member urges the engaging portion in a direction from the retracted position to the advanced position. The operation portion connected to the engaging portion to shift the engaging portion to the retracted position while resisting an urging force of the urging member. The stopper stops the operation portion to prevent a shift of the engaging portion from the retracted position to the advanced position.

A robotic surgical system according to a second aspect of the present disclosure includes a robot arm, a surgical instrument, and an adapter. The robot arm includes an attachment portion. The surgical instrument is attached to the robot arm. The adapter is attached to the attachment portion of the robot arm, and transmits a driving force from the robot arm to the surgical instrument attached to the adapter. The adapter includes: a base body that includes a first surface including an opening and attached to the robot arm, and a second surface to which the surgical instrument is attached; an engaging portion that is configured to be movable between an advanced position corresponding to the opening of the first surface and a retracted position retracted from the advanced position, and engages with the robot arm at the advanced position; an urging member that urges the engaging portion in a direction from the retracted position to the advanced position; an operation portion connected to the engaging portion to shift the engaging portion to the retracted position while resisting an urging force of the urging member; and a stopper that stops the operation portion to prevent a shift of the engaging portion from the retracted position to the advanced position.

An adapter attaching method according to a third aspect of the present disclosure is a method for attaching an adapter to a robot arm by engagement between the robot arm and an engaging portion that is movable between an advanced position corresponding to an opening formed in the adapter and a retracted position retracted from the advanced position. The engagement is made at the advanced position. The adapter attaching method includes: shifting the engaging portion to the retracted position while resisting an urging force for urging the engaging portion in a direction from the retracted position to the advanced position by operating an operation portion connected to the engaging portion; bringing the adapter into contact with the robot arm in a state where the operation portion is stopped to prevent a shift of the engaging portion from the retracted position to the advanced position using a stopper; and releasing the stop of the operation portion by the stopper to allow engagement between the adapter and the robot arm.

DETAILED DESCRIPTION

An embodiment will be hereinafter described with reference to the drawings.

(Configuration of Robotic Surgical System)

A configuration of a robotic surgical system 100 according to an embodiment will be described with reference to FIGS. 1 and 2.

Figure 1:
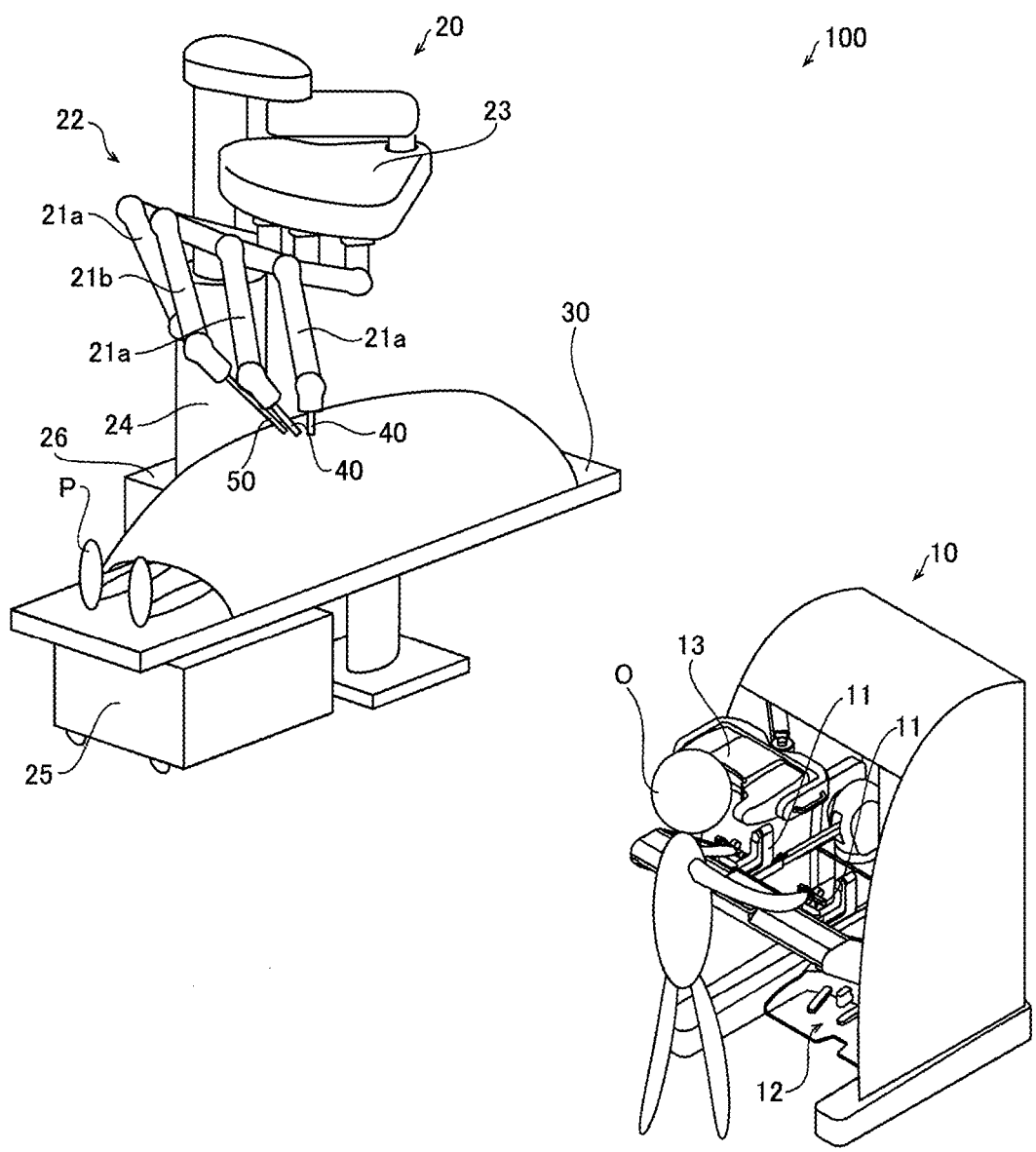
FIG. 1 is a diagram showing an outline of a robotic surgical system according to an embodiment.

As shown in FIG. 1, the robotic surgical system 100 includes a remote operation device 10 and a patient-side device 20. The remote operation device 10 is provided for remotely controlling medical equipment provided on the patient-side device 20. When an action mode command to be executed by the patient-side device 20 is input to the remote operation device 10 from an operator O who is a surgeon, the remote operation device 10 transmits the action mode command to the patient-side device 20 via a controller 26. Thereafter, the patient-side device 20 operates medical equipment such as surgical instruments 40 attached to robot arms 21a and an endoscope 50 in response to the action mode command transmitted from the remote operation device 10. In this manner, minimally invasive surgery is achieved.

The patient-side device 20 constitutes an interface with a patient P for performing an operation on the patient P. The patient-side device 20 is disposed in the vicinity of an operating table 30 on which the patient P lies. The patient-side device 20 has a plurality of robot arms, i.e., the robot arms 21a and a robot arm 21b. The endoscope 50 is attached to the robot arm 21b which is one of the robot arms, while the surgical instruments 40 are attached to the robot arms 21a which are the other robot arms.

Each of the robot arms 21a and 21b is supported by a platform 23 that is a component common to the respective arms 21a and 21b. Each of the plurality of robot arms 21a and 21b has a plurality of joints. A drive unit including a servo motor, and a position detector such as an encoder are provided on each of the joints. The robot arms 21a and 21b are configured to control the medical equipment attached to the robot arms 21a and 21b such that the medical equipment performs a desired action in accordance with a drive signal given via the controller 26.

The platform 23 is supported by a positioner 22 placed on a floor of an operating room. The positioner 22 includes a column 24 having a vertically adjustable elevating shaft and connected to a base 25 that has wheels and is movable on the floor.

The surgical instruments 40 as medical equipment are detachably attached to distal ends of the robot arms 21a. Each of the surgical instruments 40 includes a housing 43 (see FIG. 4) attached to the corresponding robot arm 21a, a shaft 42 (see FIG. 4) having an elongated shape, and an end effector 41 (see FIG. 4) provided at a distal end of the shaft 42.

Examples of the end effector 41 include grasping forceps, scissors, a hook, a high-frequency knife, a snare wire, a clamp, and a stapler. However, the end effector 41 is not limited to these examples but may be any of various treatment tools. In an operation using the patient-side device 20, the robot arm 21a associated with the operation introduces the surgical instrument 40 into the body of the patient P via a cannula (trocar) placed on the body surface of the patient P. Thereafter, the end effector 41 of the surgical instrument 40 is positioned near a surgical site.

The endoscope 50 as medical equipment is detachably attached to a distal end of the robot arm 21b.

The endoscope 50 captures an image of the inside of the body cavity of the patient P. The captured image is output to the remote operation device 10. The endoscope 50 is constituted by a 3D endoscope capable of capturing a three-dimensional image, or a 2D endoscope. In an operation using the patient-side device 20, the robot arm 21b introduces the endoscope 50 into the body of the patient P via a trocar placed on the body surface of the patient P. Thereafter, the endoscope 50 is positioned near a surgical site.

The remote operation device 10 constitutes an interface with the operator O. The remote operation device 10 is a device used by the operator O to operate the medical equipment attached to the robot arms 21a. More specifically, the remote operation device 10 is configured to transmit, to the patient-side device 20 via the controller 26, an action mode command to be executed by the surgical instrument 40 and the endoscope 50 and input by the operator O. For example, the remote operation device 10 is disposed in the vicinity of the operating table 30 for the operator to clearly view a state of the patient P even while performing a master operation. For example, the remote operation device 10 may be configured to transmit the action mode command wirelessly, and may be disposed in a separate room from the operating room where the operating table 30 is disposed.

The action mode to be executed by the surgical instrument 40 is a mode of an action (a series of positions and postures) of the surgical instrument 40, and an action achieved by an individual function of the surgical instrument 40. For example, when the surgical instrument 40 is constituted by grasping forceps, the action mode to be executed by the surgical instrument 40 is an action associated with a roll rotation position and a pitch rotation position of a wrist of the end effector 41, and an action of opening and closing a jaw. When the surgical instrument 40 is constituted by a high-frequency knife, the action mode to be executed by the surgical instrument 40 may be an oscillating action of the high-frequency knife, specifically, supply of a current to the high-frequency knife. When the surgical instrument 40 is constituted by a snare wire, the action mode to be executed by the surgical instrument 40 may be a binding action and a release action for releasing a bound state. Alternatively, this action may be an action of burning off an operation target site by supplying a current in a bipolar or monopolar manner.

The action mode to be executed by the endoscope 50 is to set the position and posture of the distal end of the endoscope 50, or the zoom magnification, for example.

Figure 2:
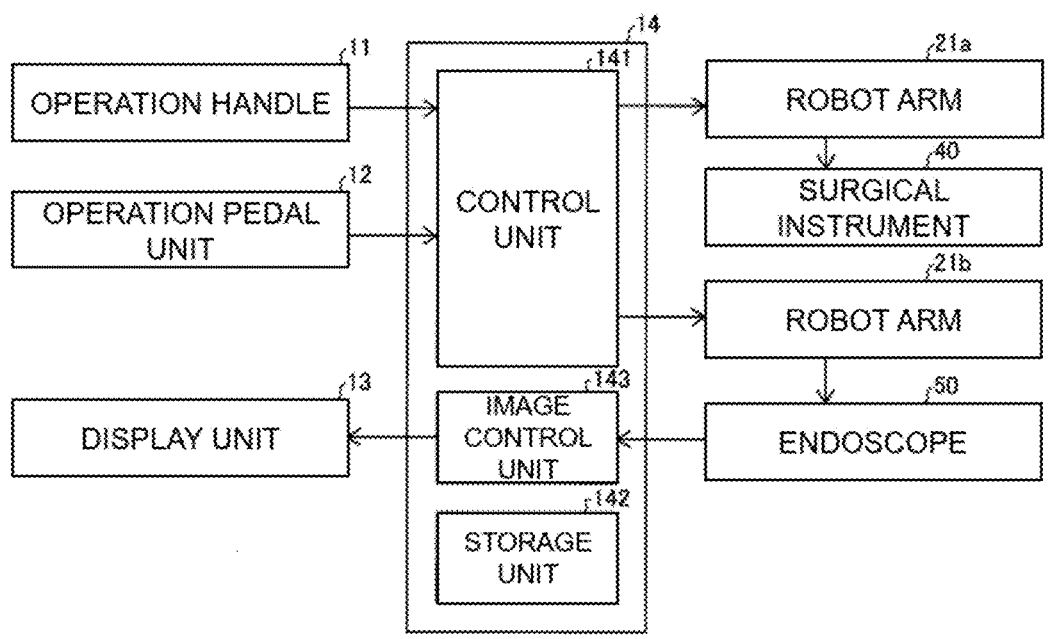
FIG. 2 is a block diagram showing a control configuration of the robotic surgical system according to the embodiment.

As shown in FIGS. 1 and 2, the remote operation device 10 includes operation handles 11, an operation pedal unit 12, a display unit 13, and a control device 14.

The operation handles 11 are provided to remotely operate the medical equipment attached to the robot arms 21*a*. Specifically, the operation handles 11 receive an operation from the operator O to operate the medical equipment (surgical instruments 40 and endoscope 50). The two operation handles 11 are provided in the horizontal direction. More specifically, one of the two operation handles 11 is operated by the right hand of the operator O, while the other of the two operation handles 11 is operated by the left hand of the operator O.

The operation handles 11 are so disposed as to extend from the rear side of the remote operation device 10 toward the front side. The operation handles 11 are configured to be movable within a predetermined three-dimensional operation area. More specifically, the operation handles 11 are configured to be movable in the up-down direction, the left-right direction, and the front-rear direction.

The remote operation device 10 and the patient-side device 20 constitute a master-slave system in controlling actions of the robot arms 21*a* and the robot arm 21*b*. More specifically, the operation handles 11 constitute an operation unit on the master side in the master-slave system, while the robot arms 21*a* and the robot arm 21*b* to which the medical equipment is attached constitute an action unit on the slave side. When the operator O operates the operation handles 11, the action of the corresponding robot arm 21*a* or robot arm 21*b* is controlled such that the distal end of the robot arm 21*a* (end effector 41 of surgical instrument 40) or the distal end of the robot arm 21*b* (endoscope 50) shifts while tracing the movement of the operation handles 11.

The patient-side device 20 is configured to control the action of the robot arm 21*a* in accordance with the set action magnification. When the action magnification is set to a magnification of ½ times larger, for example, the end effector 41 of the surgical instrument 40 is controlled so as to shift by the half of a moving distance of the operation handles 11. In this manner, a fine operation is accurately achievable.

The operation pedal unit 12 includes a plurality of pedals for executing functions associated with the medical equipment. The plurality of pedals includes a coagulation pedal, a cutting pedal, a camera pedal, and a clutch pedal. The plurality of pedals is operated by the foot of the operator O.

The coagulation pedal can perform an operation of coagulating a surgical site using the surgical instrument 40. More specifically, when the coagulation pedal is operated, a voltage for coagulation is applied to the surgical instrument 40 to coagulate the surgical site. The cutting pedal can perform an operation of cutting a surgical site using the surgical instrument 40. Specifically, when the cutting pedal is operated, a voltage for cutting is applied to the surgical instrument 40 to cut the surgical site.

The camera pedal is used for controlling the position and posture of the endoscope 50 that images the inside of the body cavity. Specifically, the camera pedal enables the operation of the endoscope 50 performed by using the operation handles 11. More specifically, the position and the posture of the endoscope 50 can be controlled using the operation handles 11 while the camera pedal is being pressed. For example, the endoscope 50 is operated with both the left and right operation handles 11. Specifically, the endoscope 50 is turned by turning the left and right operation handles 11 around a middle point of the left and right operation handles 11. When the left and right operation handles 11 are pushed together, the endoscope 50 advances toward the inside. When the left and right operation handles 11 are pulled together, the endoscope 50 returns toward the front. When the left and right operation handles 11 are shifted together in the up-down and left-right directions, the endoscope 50 shifts in the up-down and left-right directions.

The clutch pedal is used for temporarily disconnecting the operation connection between the robot arm 21*a* and the operation handles 11 to stop the operation of the surgical instrument 40. Specifically, during operation of the clutch pedal, the robot arm 21*a* of the patient-side device 20 does not act even when the operation handles 11 are operated. For example, when the operation handles 11 are operated to come close to an end of the movement range, the operation handles 11 can be returned to the vicinity of the center position of the movement range by temporarily disconnecting the operation connection in accordance with operation of the clutch pedal. When the operation of the clutch pedal is stopped, the robot arm 21*a* and the operation handles 11 are again connected to restart the operation of the operation handles 11 in the vicinity of the center position.

The display unit 13 is capable of displaying an image captured by the endoscope 50. The display unit 13 is constituted by a scope type display unit or a non-scope type display unit. The scope type display unit is a display unit of a look-in type, for example. The non-scope type display unit may include an open type display unit having a flat screen and of not a look-in type, such as a display of an ordinary personal computer.

When the scope type display unit is attached, a 3D image captured by the endoscope 50 attached to the robot arm 21*b* of the patient-side device 20 is displayed. When the non-scope type display unit is attached, a 3D image captured by the endoscope 50 provided on the patient-side device 20 is similarly displayed. When the non-scope type display unit is attached, a 2D image captured by the endoscope 50 provided on the patient-side device 20 may be displayed.

As shown in FIG. 2, the control device 14 includes a control unit 141 having an arithmetic unit such as a CPU, a storage unit 142 having a memory such as a ROM and a RAM, and an image control unit 143, for example. The control device 14 may be constituted by a single control device performing centralized control, or may be constituted by a plurality of control devices performing distributed control in cooperation with each other. The control unit 141 determines whether an action mode command input from the operation handles 11 is an action mode command to be executed by the robot arm 21*a*, or an action mode command to be executed by the endoscope 50 in accordance with a switching state of the operation pedal unit 12. Upon determining that the action mode command input to the operation handles 11 is an action mode command to be executed by the surgical instrument 40, the control unit 141 transmits the action mode command to the corresponding robot arm 21*a*. In this manner, the robot arm 21*a* is driven to control the action of the surgical instrument 40 attached to the robot arm 21*a*.

Upon determining that the action mode command input to the operation handles 11 is an action mode command to be executed by the endoscope 50, the control unit 141 transmits the action mode command to the robot arm 21*b*. In this manner, the robot arm 21*b* is driven to control the action of the endoscope 50 attached to the robot arm 21*b*.

For example, control programs corresponding to the types of the surgical instrument 40 are stored in the storage unit 142. The control unit 141 reads these control programs in accordance with the types of the attached surgical instrument 40 to perform actions suited for the individual surgical instruments 40 based on the action command of the operation handles 11 and/or the operation pedal unit 12 of the remote operation device 10.

The image control unit 143 transmits an image captured by the endoscope 50 to the display unit 13. The image control unit 143 retouches the image as necessary.

(Configurations of Adapter and Surgical Instrument)

The configurations of an adapter 60 and the surgical instrument 40 according to the embodiment will be described with reference to FIGS. 3 to 15.

Figure 3:
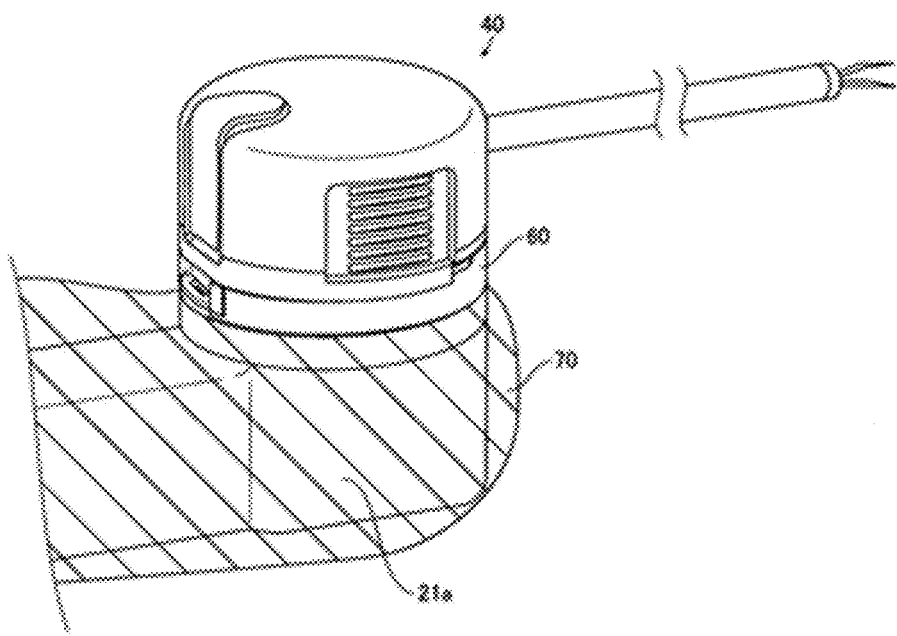
FIG. 3 is a perspective view showing a state where a surgical instrument is attached to a robot arm according to the embodiment via an adapter.

As shown in FIG. 3, the robot arm 21a (21b) is covered with a drape 70 for use in a clean area. In the operating room, a clean operation is performed to prevent contamination of an incised portion and medical devices by pathogenic bacteria, foreign substances, and the like as a result of an operation. In this clean operation, a clean area and a contaminated area other than the clean area are defined. A surgical site is located in the clean area. During an operation, members of a surgical team, including the operator O, ensure that only sterilized objects are located in the clean area, and sterilize an object located in the contaminated area when this object is to be shifted to the clean area. Similarly, when the members of the surgical team including operator O place their hands in the contaminated area, the hands are sterilized before directly contacting an object located in the clean area. Instruments used in the clean area are sterilized or covered with the sterilized drape 70.

The drape 70 is disposed between the robot arm 21a and the surgical instrument 40. Specifically, the drape 70 is disposed between the adapter 60 and the robot arm 21a. The adapter 60 is attached to an attachment portion 211 of the robot arm 21a via the drape 70. That is, the adapter 60 is a drape adapter used to insert the drape 70 between the adapter 60 and the robot arm 21a. The surgical instrument 40 is attached to the adapter 60. The robot arm 21a transmits power to the surgical instrument 40 via the adapter 60 to drive the end effector 41 of the surgical instrument 40.

Figure 4:
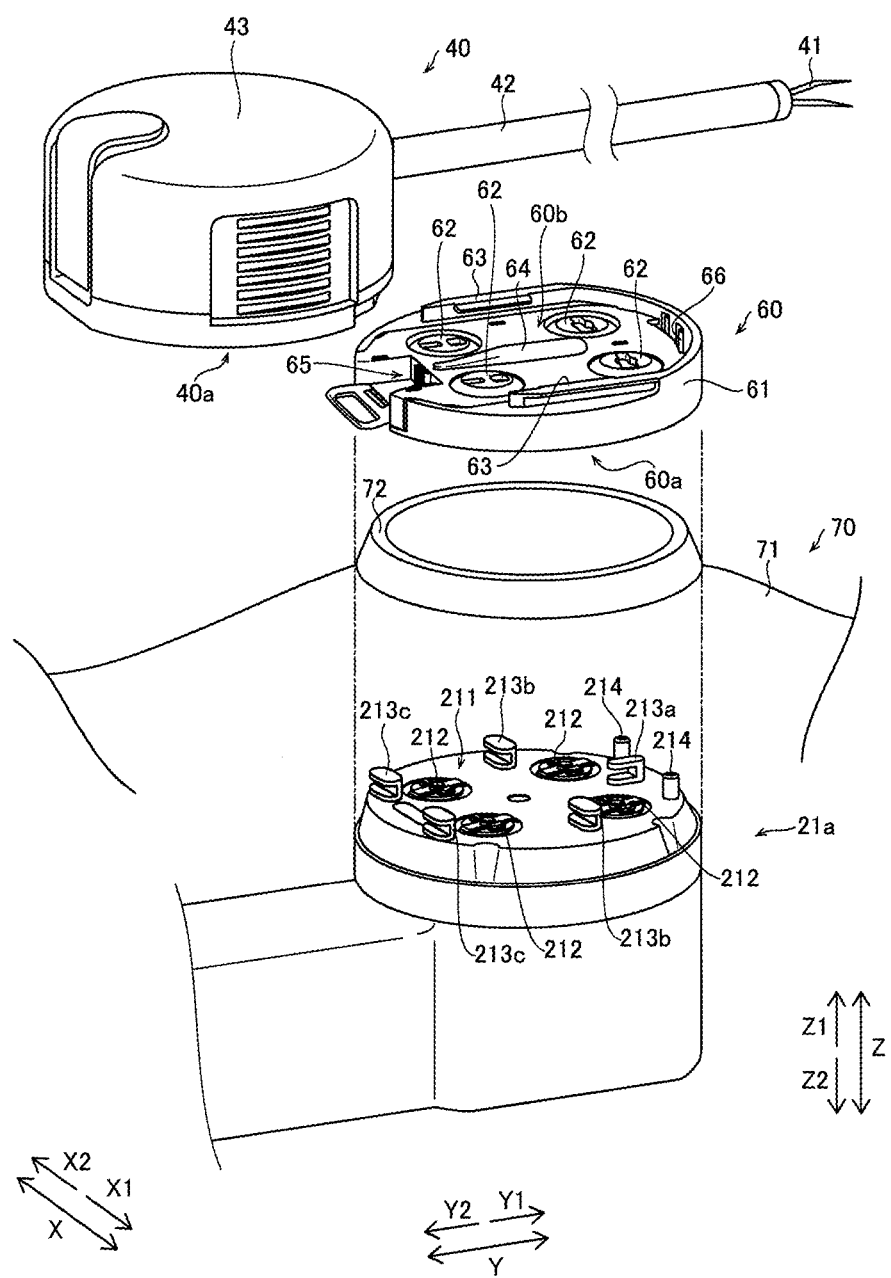
FIG. 4 is a perspective view showing a state where the adapter and the surgical instrument are removed from the robot arm according to the embodiment.
Figure 5:
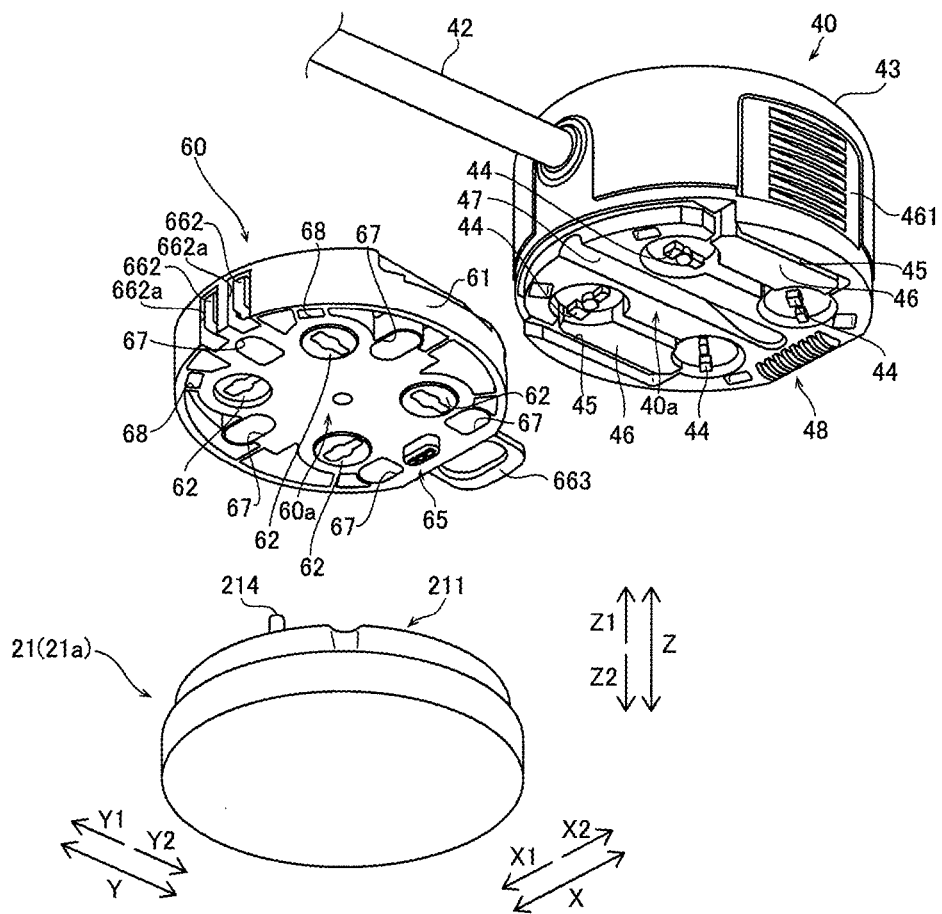
FIG. 5 is a perspective view of the adapter, the surgical instrument, and an attachment portion of the robot arm according to the embodiment as viewed from below.

As shown in FIG. 4, the adapter 60 includes a base body 61, a plurality of drive transmission members 62, guide rails 63, a preceding guide rail 64, an electrode array 65, and an arm engaging portion 66. As shown in FIG. 5, the adapter 60 further includes a plurality of openings 67 and a plurality of positioning holes 68. The adapter 60 has a first surface 60a disposed on a Z2 side and attached to the robot arm 21a. The adapter 60 further has a second surface 60b disposed on a Z1 side as a surface to which the surgical instrument 40 is attached.

As shown in FIG. 5, an attachment surface 40a disposed on the Z2 side of the housing 43 of the surgical instrument 40 is attached to the adapter 60. The surgical instrument 40 includes a plurality of driven portions 44, two guide grooves 45, two movable members 46, a preceding guide groove 47, and an electrode array 48.

As shown in FIG. 4, the drape 70 includes a main body 71 and an attachment portion 72. The main body 71 has a film shape. The attachment portion 72 is formed by resin molding. The attachment portion 72 has a through hole at an engaging portion between the robot arm 21a and the adapter 60. The through hole may be provided for each of engaging portions. Alternatively, the through hole may be provided so as to correspond to a plurality of engaging portions.

The adapter 60 is attached to the attachment portion 211 of the robot arm 21a. The attachment portion 211 of the robot arm 21a includes drive members 212, engaging protrusions 213a, 213b, and 213c, and bosses 214. The two engaging protrusions 213b and the two engaging protrusions 213c are provided.

Each of the engaging protrusions 213a, 213b, and 213c includes a groove 2131. The engaging protrusions 213a, 213b, and 213c are provided to engage with the adapter 60. More specifically, engaging portions 661a, 661b, and 661c of the adapter 60 engage with the grooves 2131 of the engaging protrusions 213a, 213b, and 213c of the robot arm 21a, respectively. Each of the plurality of grooves 2131 is configured to open in a Y2 direction.

As shown in FIG. 5, the plurality of driven portions 44 of the surgical instrument 40 is rotated to drive the end effector 41. Specifically, the driven portions 44 and the end effector 41 are connected to each other by wires inserted into the shaft 42. The wires are pulled in accordance with rotations of the driven portions 44 to drive the end effector 41. The driven portions 44 are connected to the shaft 42 by a gear within the housing 43. The shaft 42 is rotated in accordance with rotations of the driven portions 44.

For example, the four driven portions 44 are provided. The shaft 42 is rotated by a rotation of one of the driven portions 44. The end effector 41 is driven by rotations of the other three driven portions 44. Two of the four driven portions 44 are arranged in the X direction, and the remaining two driven portions 44 are arranged in the Y direction.

The guide grooves 45 are configured to extend in the Y direction. The two guide grooves 45 are provided so as to face each other in the X direction. The two guide grooves 45 are provided substantially in parallel. The guide grooves 45 are grooves into which the guide rails 63 of the adapter 60 are inserted to guide attachment to the adapter 60. The width of each of the guide grooves 45 changes as the corresponding movable member 46 shifts in the X direction. Specifically, the width of each of the guide grooves 45 increases by an inward shift of the corresponding movable member 46. In addition, the width of each of the guide grooves 45 decreases by an outward shift of the corresponding movable member 46. Each of the movable members 46 is urged in a direction of reducing the width of the corresponding guide groove 45 (outward direction). Specifically, each of the movable members 46 is urged by a spring. When the operator presses a button 461, each of the movable members 46 moves in the direction of increasing the width of the corresponding guide groove 45 (inward direction).

The preceding guide groove 47 is configured to extend in the Y direction. The preceding guide groove 47 is formed between the two guide grooves 45. The preceding guide groove 47 is configured to extend substantially in parallel to the two guide grooves 45. The preceding guide groove 47 is provided substantially at the center of the attachment surface 40a in the X direction.

The electrode array 48 is connected to the robot arm 21a via the electrode array 65 of the adapter 60. The electrode array 48 is connected to a substrate provided within the housing 43. More specifically, the substrate of the surgical instrument 40 and the robot arm 21a are connected by attaching the surgical instrument 40 to the robot arm 21a via the adapter 60. The substrate within the housing 43 is used for management of the type of the surgical instrument 40 and the number of times of use of the surgical instrument 40, for example.

Figure 6:
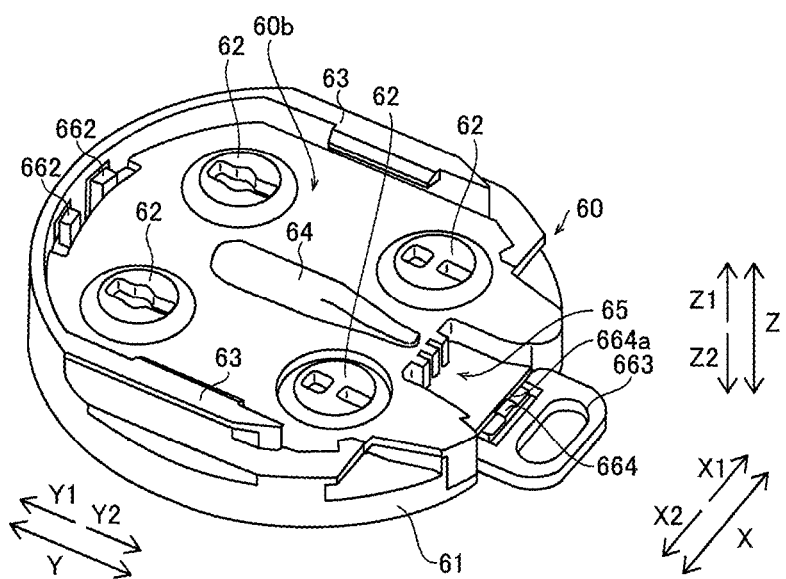
FIG. 6 is a perspective view of the adapter according to the embodiment as viewed from above.

As shown in FIGS. 4 to 6, the adapter 60 is provided for detachably connecting the surgical instrument 40 to the robot arm 21a of the robotic surgical system 100. The base body 61 includes the first surface 60a for attachment to the robot arm 21a, and the second surface 60b to which the attachment surface 40a of the surgical instrument 40 is attached. The adapter 60 is detachably attached to the robot arm 21a. The adapter 60 transmits a driving force from the robot arm 21a to the surgical instrument 40.

Figure 9:
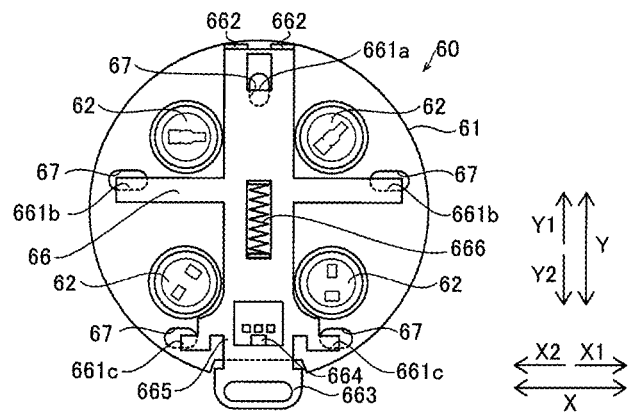
FIG. 9 is a first plan view for explaining attachment of the adapter to the robot arm according to the embodiment.
Figure 10:
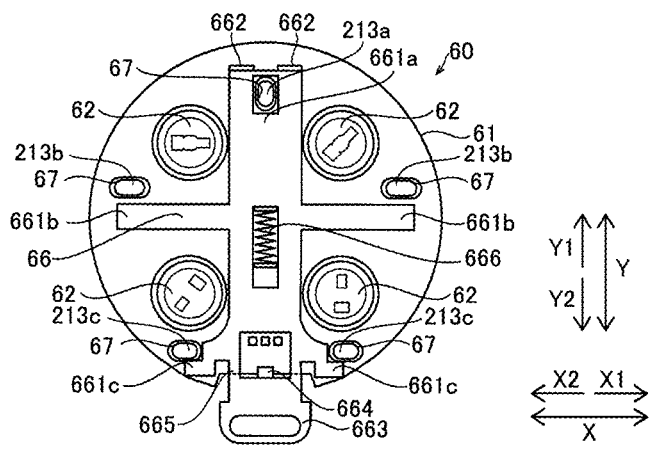
FIG. 10 is a second plan view for explaining attachment of the adapter to the robot arm according to the embodiment.
Figure 11:
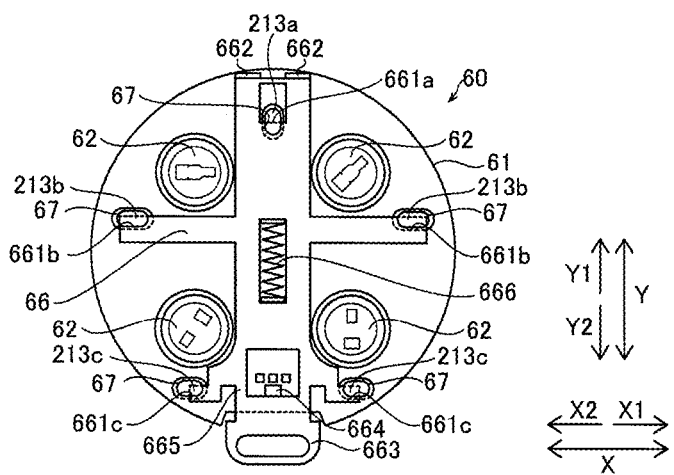
FIG. 11 is a third plan view for explaining attachment of the adapter to the robot arm according to the embodiment.

The drive transmission members 62 are rotatably provided on the base body 61. Specifically, the drive transmission members 62 are provided rotatably around a rotation axis extending in the Z direction. Specifically, the drive transmission members 62 are provided rotatably around the rotation axis perpendicular to the first surface 60a and the second surface 60b. The drive transmission members 62 transmit rotations of the plurality of drive members 212 provided on the attachment portion 211 of the robot arm 21a to the plurality of driven portions 44 provided on the surgical instrument 40. A plurality of the drive transmission members 62 is provided in correspondence with the drive members 212 of the robot arm 21a and the driven portions 44 of the surgical instrument 40. The plurality of drive transmission members 62 is disposed at positions corresponding to the drive members 212 of the robot arm 21a and the driven portions 44 of the surgical instrument 40. As shown in FIGS. 9 to 11, the drive transmission members 62 are rotatably provided at portions other than an area where the engaging portions 661a to 661c, an operation portion 663, and a stopper 664 of the base body 61 are disposed.

As shown in FIG. 6, the guide rails 63 are provided on the second surface 60b. The guide rails 63 are configured to extend in the Y direction. The two guide rails 63 are provided so as to face each other in the X direction. The two guide rails 63 are provided substantially in parallel. The two guide rails 63 are provided in correspondence with the two guide grooves 45 disposed substantially in parallel on the attachment surface 40a of the surgical instrument 40. The guide rails 63 of the second surface 60b are each configured to slide in correspondence with the guide grooves 45 of the attachment surface 40a to guide with correspondence between the plurality of drive transmission members 62 and the plurality of driven portions 44 provided on the attachment surface 40a.

The preceding guide rail 64 is provided on the second surface 60b. The preceding guide rail 64 is configured to extend in the Y direction. The preceding guide rail 64 is provided between the two guide rails 63. The preceding guide rail 64 is configured to extend substantially in parallel to the two guide rails 63. The preceding guide rail 64 is provided substantially at the center of the second surface 60b in the X direction. The preceding guide rail 64 is provided in correspondence with the preceding guide groove 47 formed in the attachment surface 40a. Accordingly, the preceding guide rail 64 guides the surgical instrument 40 ahead of the two guide rails 63.

The electrode array 65 is connected to the electrode array 48 of the surgical instrument 40 and the robot arm 21a.

Figure 8:
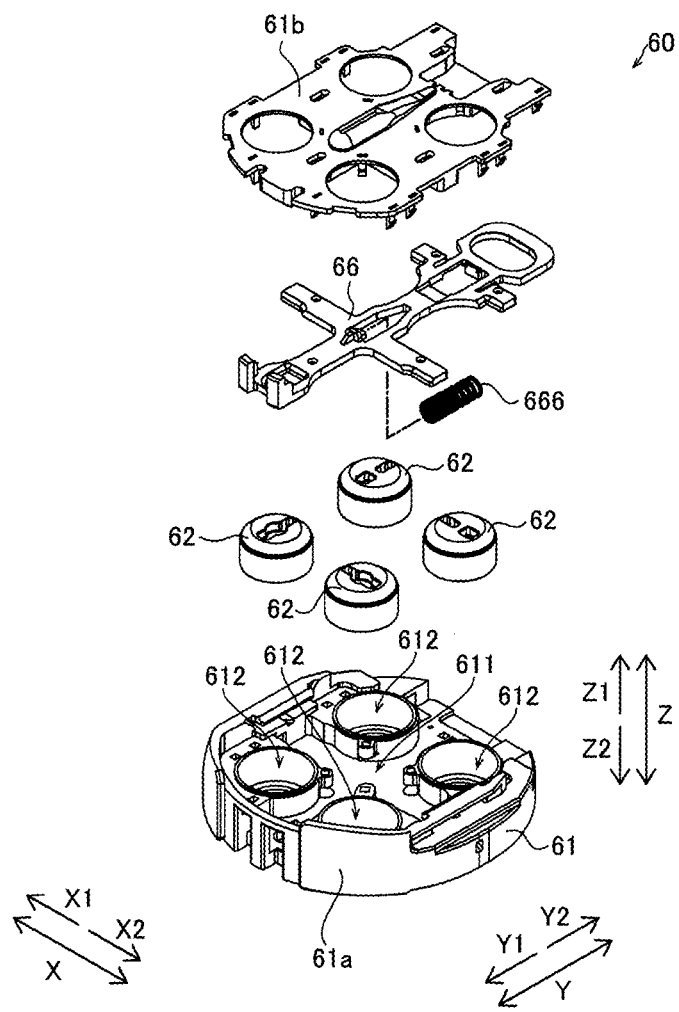
FIG. 8 is an exploded perspective view of the adapter according to the embodiment.

As shown in FIG. 8, the base body 61 includes a first base member 61a on the first surface 60a side (Z2 side) and a second base member 61b on the second surface 60b side (Z1 side). The first base member 61a has cylindrical portions 612 where the drive transmission members 62 are disposed, and a space 611 where the arm engaging portion 66 is disposed. The first base member 61a and the second base member 61b are connected by engagement with each other. The first base member 61a has a plurality of the openings 67 (see FIG. 5). The openings 67 are through holes penetrating the first base member 61a in the Z direction. The second base member 61b is disposed so as to cover the arm engaging portion 66 disposed in the space 611.

As shown in FIGS. 9 to 11, the arm engaging portion 66 engages with the engaging protrusions 213a to 213c of the robot arm 21a. Specifically, the arm engaging portion 66 engages with the engaging protrusions 213a to 213c inserted in the Z direction into the openings 67 formed in the first surface 60a. The arm engaging portion 66 includes the engaging portions 661a, 661b, and 661c, regulation portions 662, the operation portion 663, the stopper 664, and a connection portion 665. The arm engaging portion 66 is urged in the Y1 direction by an urging member 666. The two engaging portions 661b and the two engaging portions 661c are provided.

The engaging portions 661a to 661c of the arm engaging portion 66 are configured to be movable relative to the base body 61 in a predetermined direction. Specifically, the engaging portions 661a to 661c are movable relative to the base body 61 in the Y direction. The engaging portions 661a to 661c are shifted in the Y1 direction to engage with the engaging protrusions 213a to 213c, respectively. On the other hand, the arm engaging portion 66 is shifted in the Y2 direction to release engagement with the engaging protrusions 213a to 213c. According to the present embodiment, each of the engaging portions 661a to 661c is movable between an advanced position (see FIGS. 9 and 11) advanced in a direction (Y direction) crossing a direction (Z direction) where the first surface 60a and the attachment portion 211 of the robot arm 21a face each other, and a retracted position (see FIG. 10) retracted from the plurality of openings 67. The urging member 666 urges the engaging portions 661a to 661c in a direction (Y1 direction) from the retracted position to the advanced position.

In this manner, switching between the engaged state and the released state is achievable by shifting the engaging portions 661a to 661c in a direction crossing the direction where the first surface 60a and the attachment portion 211 of the robot arm 21a face each other (in a direction (Y direction) extending along the first surface 60a and different from the engagement direction (Z direction) between the adapter 60 and the robot arm 21a).

The regulation portions 662 are connected to the engaging portions 661a to 661c and the operation portion 663. When the surgical instrument 40 is attached to the second surface 60b, the regulation portions 662 contact the surgical instrument 40 to regulate shifts of the engaging portions 661a to 661c. In this manner, release of the engagement between the robot arm 21a and the adapter 60 can be suppressed when the surgical instrument 40 is attached. Therefore, separation of the surgical instrument 40 from the robot arm 21a together with the adapter 60 can be suppressed.

Specifically, the regulation portions 662 are configured to protrude toward the surgical instrument 40. The regulation portions 662 are configured to contact the surgical instrument 40 to regulate a shift of the surgical instrument 40 when the surgical instrument 40 is attached to the second surface 60b. More specifically, when the surgical instrument 40 is slid in the Y direction and attached to the adapter 60, a Y1-side end of the housing 43 of the surgical instrument 40 comes into contact with the regulation portions 662. The surgical instrument 40 fixed to the adapter 60 is not allowed to shift in the Y direction. Therefore, a shift of the regulation portions 662 in the Y direction is also regulated. In this manner, the shift of the regulation portions 662 can be regulated by the surgical instrument 40 when the surgical instrument 40 is attached. Therefore, a member for regulating the shift of the regulation portions 662 need not be separately provided.

Figure 7:
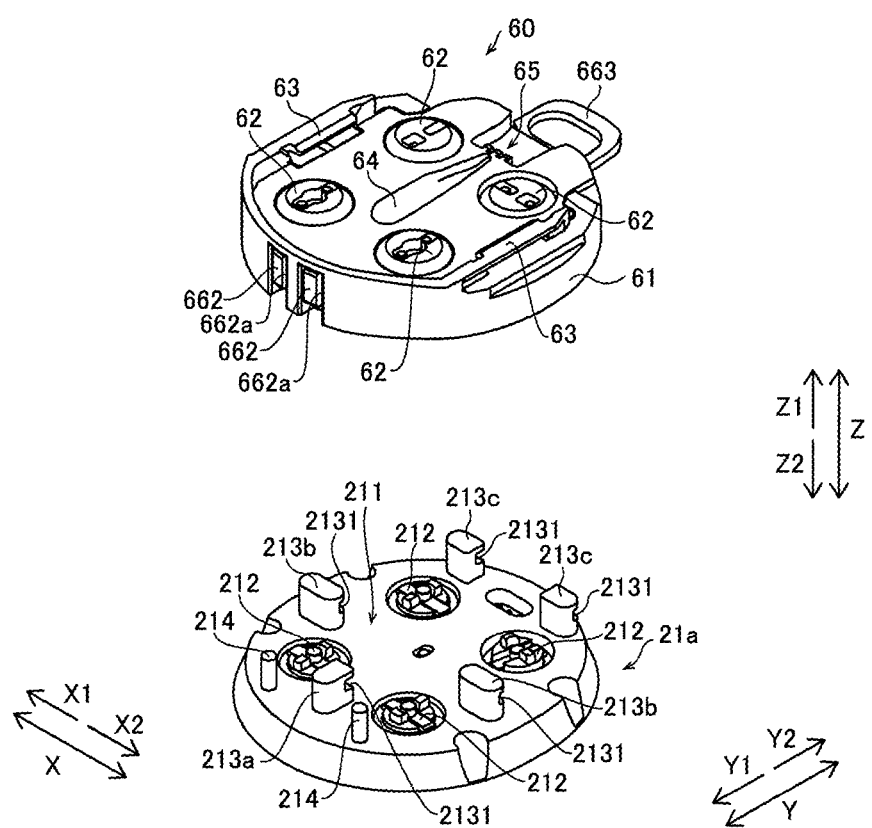
FIG. 7 is a perspective view showing a state where the adapter is removed from the attachment portion of the robot arm according to the embodiment.

As shown in FIGS. 5 and 7, the base body 61 includes openings 662a where the regulation portions 662 are disposed when the engaging portions 661a to 661c are shifted to the advanced positions. Each of the openings 662a has an elongated shape and is formed in an outer circumferential surface of the base body 61. In this case, a shift of the engaging portions 661a to 661c toward the advanced positions can be easily confirmed by checking that the regulation portions 662 are located in the openings 662a. Moreover, the elongated shape of the openings 662a suppresses contact between a finger or the like having entered the openings 662a and the regulation portions 662. This can suppress an erroneous operation of a shift of the regulation portions 662 caused by the contact between the finger or the like and the regulation portions 662 via the openings 662a.

As shown in FIGS. 10 and 11, the engaging protrusion 213a provided near a Y1-side end of the attachment portion 211 of the robot arm 21a in the Y direction engages with the engaging portion 661a provided near a Y1-side end of the arm engaging portion 66 in the Y direction. The two engaging protrusions 213b provided near the center of the attachment portion 211 of the robot arm 21a in the Y direction engage with the corresponding two engaging portions 661b provided near the center of the arm engaging portion 66 in the Y direction. The two engaging protrusions 213c provided near a Y2-side end of the attachment portion 211 of the robot arm 21a in the Y direction engage with the two engaging portions 661c provided near a Y2-side end of the arm engaging portion 66 in the Y direction.

The engaging portions 661a to 661c, the operation portion 663, and the stopper 664 are formed integrally with each other. As a result, reduction of the number of components, and simplification of the configuration are achievable in comparison with a case where the engaging portions 661a to 661c, the operation portion 663, and the stopper 664 are separately provided.

The arm engaging portion 66 includes the engaging portions 661a to and 661c, the regulation portions 662, the operation portion 663, the stopper 664, and the connection portion 665 formed integrally with each other. The arm engaging portion 66 is made of a resin material, for example. As a result, the plurality of engaging portions 661a to 661c moves as one body in accordance with a shift of the operation portion 663.

The engaging portions 661a to 661c may be configured to bend in a direction from the advanced positions to the retracted positions. In this case, dimensional accuracy of the engaging portions 661a to 661c can be absorbed by bending, and therefore engagement of the engaging portions 661a to 661c is achievable while reducing backlash.

The operation portion 663 is connected to the engaging portions 661a to 661c. The operation portion 663 is provided to shift the engaging portions 661a to 661c to the retracted positions while resisting an urging force of the urging member 666. The operation portion 663 is pulled in the Y2 direction by the operator during operation. The operation portion 663 is provided at a Y2-side end of the arm engaging portion 66. The operation portion 663 is provided to shift the engaging portions 661a to 661c in the Y2 direction and release the engagement state in accordance with pulling of the operation portion 663 in the Y2 direction by the operator.

The operation portion 663 moves the plurality of engaging portions 661a to 661c as one piece body. In this manner, the engagement state and the release state of the plurality of engaging portions 661a to 661c can be collectively switched by operating the common operation portion 663.

According to the present embodiment, the stopper 664 stops the operation portion 663 to prevent a shift of the engaging portions 661a to 661c from the retracted positions to the advanced positions. In this case, the position of the operation portion 663 can be maintained by the stopper 664 in a state where the operation portion 663 has been shifted to locate the engaging portions 661a to 661c of the adapter 60 at the retracted positions in advance. Therefore, a force such as bending need not be applied at the time of engagement of the adapter 60 with the robot arm 21a. More specifically, an action of applying a force and an action of bringing the adapter 60 into engagement with the robot arm 21a can be separately performed. Therefore, the adapter 60 can be easily attached to and detached from the robot arm 21a in comparison with a case where the adapter 60 engages with the robot arm 21a with a force applied. Moreover, the engaging portions 661a to 661c can be shifted to the advanced positions using the urging member 666 by releasing the stopper 664 in a state where the adapter 60 is in contact with the robot arm 21a. As a result, the adapter 60 can be easily attached to and detached from the robot arm 21a.

The stopper 664 is configured to switch between a state of stopping the operation portion 663 and a state of releasing the stop of the operation portion 663 by shifting the engaging portions 661a to 661c in a direction (Z direction) orthogonal to a predetermined direction (Y direction) where the engaging portions 661a to 661c are movable. In this manner, the state of stopping the operation portion 663 and the state of releasing the stop of the operation portion 663 can be switched by shifting the stopper 664 in the direction orthogonal to the direction of urging the engaging portions 661a to 661c (operation portion 663) using the urging member 666. Therefore, the operation portion 663 need not be operated in the direction of resisting the urging force of the urging member 666 at the time of switching from the state of stopping the operation portion 663 to the state of releasing the stop. This can suppress an increase in the force required for switching the state of the stopper 664. Therefore, the state of the stopper 664 for stopping the operation portion 663 and the state of the stopper 664 for releasing the stop of the operation portion 663 can be easily switched.

Specifically, the stopper 664 is configured to switch between the state of stopping the operation portion 663 and the state of releasing the stop of the operation portion 663 by shifting the engaging portions 661a to 661c in a direction where the first surface 60a and the second surface 60b are arranged (Z direction) in the direction orthogonal to the predetermined direction (Y direction) where the engaging portions 661a to 661c are movable. This makes it possible to easily stop the operation portion 663 by engagement between the stopper 664 and a member on the second surface 60b side.

The stopper 664 is configured to protrude toward the second surface 60b. The stopper 664 is also configured to engage with a stopping portion 664a (see FIG. 6) provided on a circumferential portion of a member of the base body 61 on the second surface 60b side (second base member 61b) to stop the operation portion 663. In this case, at the time of attachment of the adapter 60 to the robot arm 21a, the stopper 664 is moved in a direction toward the robot arm 21a by an inertial force or an impact produced when the adapter 60 comes into contact with the robot arm 21a and stops. Therefore, the state of the stop of the operation portion 663 by the stopper 664 can be automatically released without performing an operation of shifting the stopper 664. In this manner, the adapter 60 can be more easily attached to and detached from the robot arm 21*a*. That is, the stopper 664 is configured to move in such a manner as to release the engagement with the stopping portion 664*a* at the time of attachment to the robot arm 21*a*. For example, the stopper 664 protrudes toward the second surface 60*b* by a length approximately in a range of 0.5 mm to 2 mm inclusive.

The stopper 664 is also configured to shift by a bending deformation of the connection portion 665 provided between the operation portion 663 and the engaging portions 661*a* to 661*c* to switch between the state of stopping the operation portion 663 and the state of releasing the stop of the operation portion 663. In this case, the state of the stopper 664 can be switched only by the bend of the connection portion 665. Therefore, the structure does not become complicated.

The urging member 666 is disposed substantially at the center of the adapter 60 as viewed in the Z direction. The urging member 666 urges the engaging portions 661*a* to 661*c* in the Y1 direction. For example, the urging member 666 is constituted by a spring.

As shown in FIG. 5, a plurality of the openings 67 is formed in the first surface 60*a* of the base body 61. That is, the adapter 60 is fixed to the robot arm 21*a* at a plurality of engagement portions. For example, the five openings 67 are formed. The plurality of openings 67 is disposed at substantially equal intervals on the outer circumference side of the first surface 60*a*.

The positioning holes 68 are formed in the first surface 60*a*. The bosses 214 of the robot arm 21*a* fit into the positioning holes 68. A plurality of the positioning holes 68 is formed. The positioning holes 68 are formed near a Y1-side end of the first surface 60*a*.

Figure 12:
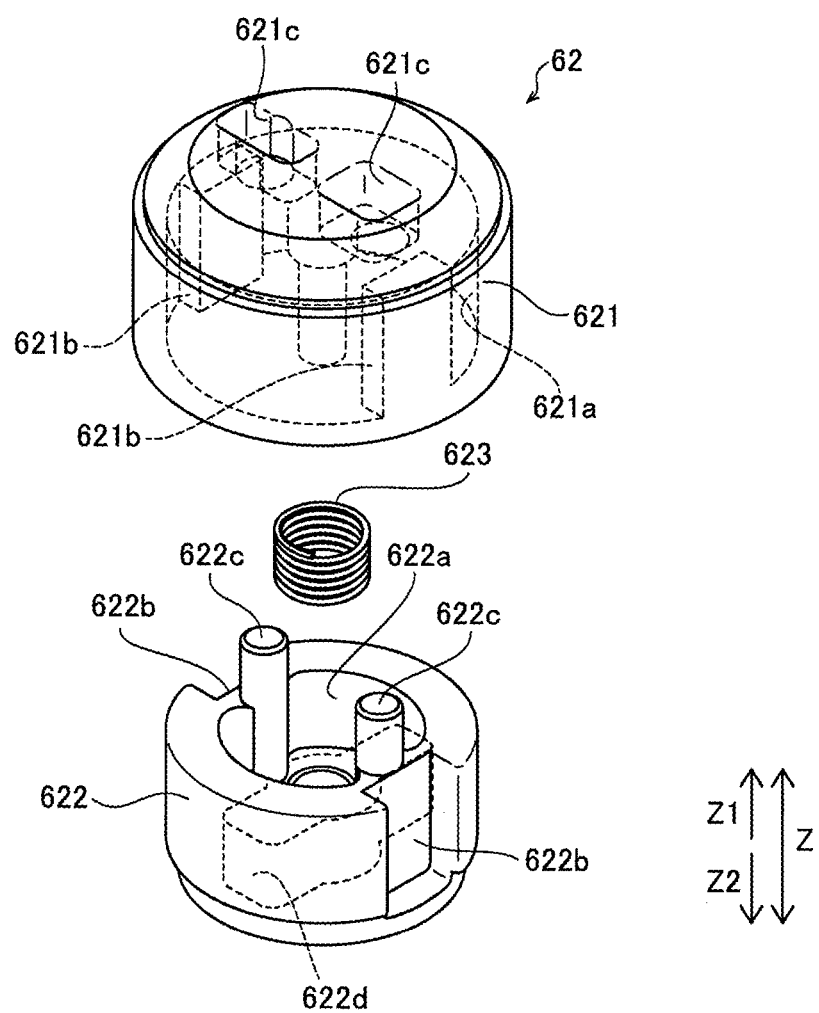
FIG. 12 is an exploded perspective view of a drive transmission member of the adapter according to the embodiment.

As shown in FIG. 12, each of the drive transmission members 62 includes a first member 621, and a second member 622 movable relative to the first member 621 via an urging member 623. The first member 621 includes a recess 621*a* into which the second member 622 fits, and engaging portions 621*b* engaging with the second member 622. The first member 621 further includes engaging portions 621*c* engaging with the driven portions 44 of the surgical instrument 40. The second member 622 includes a recess 622*a* in which the urging member 623 is accommodated, and engaging portions 622*b* engaging with the first member 621. The second member 622 further includes projections 622*c* engaging with the first member 621. The second member 622 further includes an engaging portion 622*d* engaging with the drive member 212 of the robot arm 21*a*.

The first member 621 and the second member 622 are fitted to each other in the Z direction with the urging member 623 interposed between the first member 621 and the second member 622. The first member 621 is disposed on the second surface 60*b* side (Z1 side). The second member 622 is disposed on the first surface 60*a* side (Z2 side). The urging member 623 urges the first member 621 toward the Z1 side with respect to the second member 622. For example, the urging member 623 is constituted by a spring.

(Attachment of Adapter to Robot Arm)

The attachment of the adapter 60 to the robot arm 21*a* according to the embodiment will be described with reference to FIGS. 9 to 11 and FIGS. 13 to 15.

Figure 13:
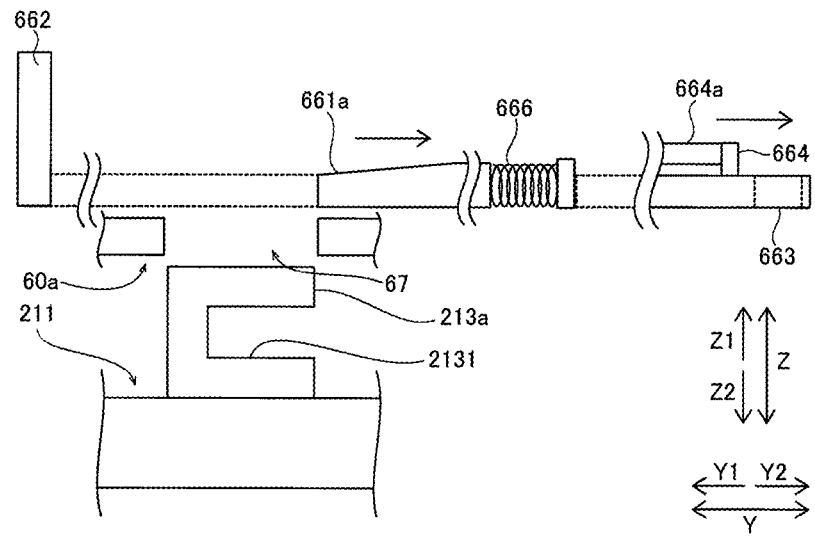
FIG. 13 is a diagram showing a state where an engaging portion of the adapter according to the embodiment is shifted to a retracted position.

As shown in FIGS. 10 and 13, the engaging portions 661*a* to 661*c* are shifted to the retracted positions while resisting the urging force for urging the engaging portions 661*a* to 661*c* from the retracted positions to the advanced positions by operating the operation portion 663 connected to the engaging portions 661*a* to 661*c*. In this manner, a space on the second surface 60*b* side of the plurality of openings 67 (Z1 direction) is opened.

The operation portion 663 is stopped by the stopper 664 to prevent shifts of the engaging portions 661*a* to 661*c* from the retracted positions to the advanced positions. Specifically, the stopper 664 is brought into engagement with the stopping portion 664*a*.

Subsequently, as shown in FIG. 10, the adapter 60 is brought into contact with the robot arm 21*a* in a state where the operation portion 663 is stopped by the stopper 664 to prevent shifts of the engaging portions 661*a* to 661*c* from the retracted positions to the advanced positions.

Figure 14:
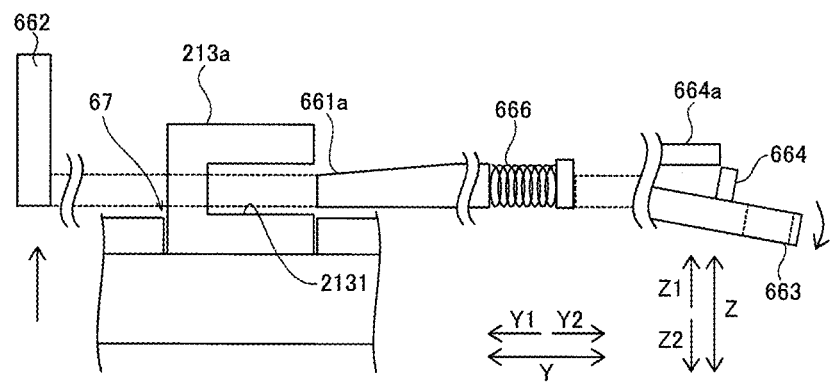
FIG. 14 is a diagram showing a state where a shift of an operation portion achieved by a stopper of the adapter according to the embodiment has been released.
Figure 15:
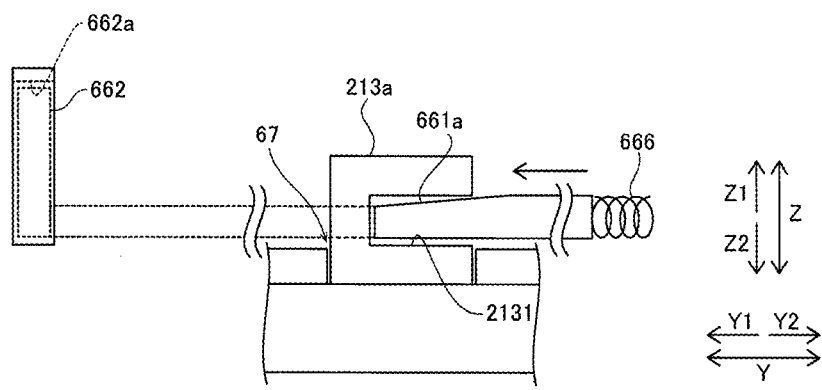
FIG. 15 is a diagram showing a state where the engaging portion of the adapter according to the embodiment is shifted to an advanced position.

Thereafter, as shown in FIG. 14, the stop of the operation portion 663 by the stopper 664 is released. After the release of the stop, the adapter 60 (engaging portions 661*a*, 661*b*, 661*c*) is brought into engagement with the robot arm 21*a* (engaging protrusions 213*a*, 213*b*, 213*c*) as shown in FIGS. 11 and 15.

(Attachment of Surgical Instrument to Robot Arm)

Attachment of the surgical instrument 40 to the robot arm 21*a* according to the embodiment will be described with reference to FIGS. 16 to 18.

Figure 16:
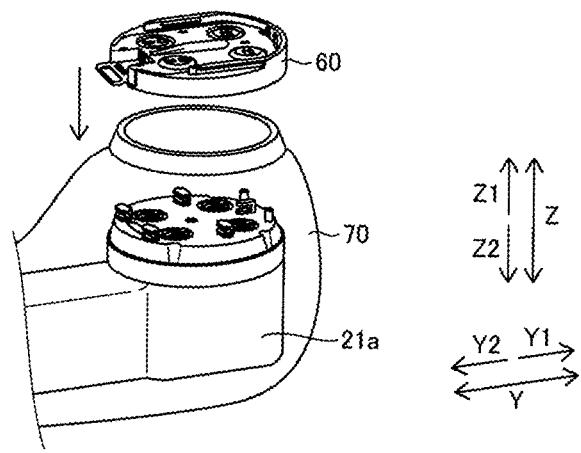
FIG. 16 is a diagram for explaining attachment of the adapter to the robot arm according to the embodiment.

As shown in FIG. 16, the adapter 60 is attached to the robot arm 21*a*, which is covered with the drape 70. The adapter 60 is shifted in the Z direction with respect to the robot arm 21*a*, and attached to the robot arm 21*a*. More specifically, the adapter 60 is shifted in a direction (Z direction) perpendicular to the first surface 60*a* and the second surface 60*b*, and attached to the attachment portion 211 of the robot arm 21*a*.

Figure 17:
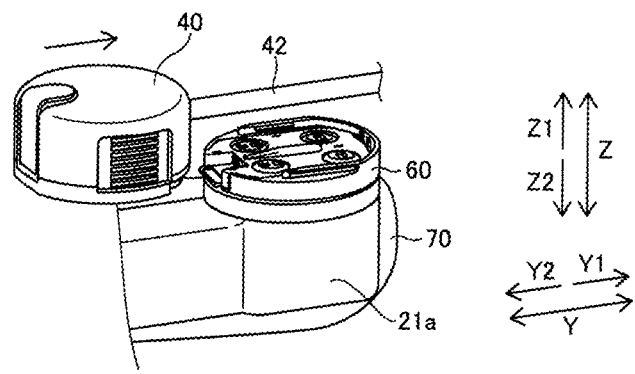
FIG. 17 is a first diagram for explaining attachment of the surgical instrument to the adapter according to the embodiment.
Figure 18:
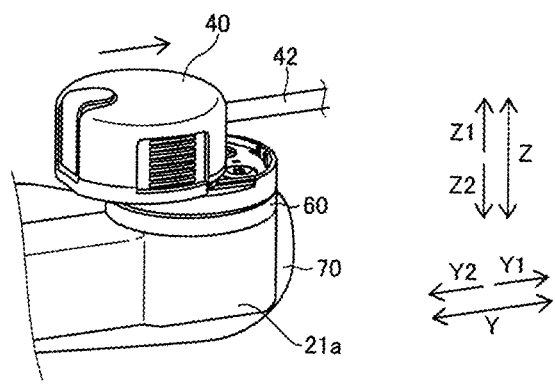
FIG. 18 is a second diagram for explaining attachment of the surgical instrument to the adapter according to the embodiment.

As shown in FIGS. 17 and 18, the surgical instrument 40 is attached to the adapter 60 attached to the robot arm 21*a*. The surgical instrument 40 is moved in the Y direction along the preceding guide rail 64 and the two guide rails 63 of the adapter 60, and attached to the adapter 60. In this manner, the surgical instrument 40 is attached to the robot arm 21*a* via the adapter 60.

For removing the surgical instrument 40 from the robot arm 21*a*, the surgical instrument 40 is slid in the Y2 direction with a press of the button 461 of the movable member 46 of the surgical instrument 40 to remove the surgical instrument 40 from the adapter 60.

For removing the adapter 60 from the robot arm 21*a*, the operation portion 663 is pulled in the Y2 direction in a state where the surgical instrument 40 has been removed from the adapter 60 to release the engagement between the adapter 60 and the robot arm 21*a*. In this state, the adapter 60 is moved in the Z1 direction to be removed from the robot arm 21*a*.

Modified Examples

It should be noted that the present disclosure is not limited to the embodiment disclosed herein, and has been described by way of example in all aspects. The scope of the present disclosure is defined not by the above description of the embodiment but by the appended claims, and includes all modifications (modified examples) within the meanings and the range equivalent to the claims.

For example, in the configuration example of the embodiment described above, the adapter and the attachment portion of the robot arm engage with each other at five positions using the engaging portions. However, the present disclosure is not limited to this example. According to the present disclosure, the number of the positions of the engagement between the adapter and the attachment portion of the robot arm by the engaging portions may be any number other than five as long as the engagement is made at a plurality of positions.

In the configuration example of the embodiment described above, switching between the state of stopping the operation portion of the stopper and the state of releasing the stop of the operation portion is achieved by a shift of the stopper in the direction where the first surface and the second surface are arranged in the direction orthogonal to the predetermined direction where the engaging portions are movable. However, the present disclosure is not limited to this example. According to the present disclosure, switching between the state of stopping the operation portion of the stopper and the state of releasing the stop of the operation portion may be achieved by shifting the stopper in a direction (X direction) parallel to the first surface and the second surface in the direction orthogonal to the predetermined direction where the engaging portions are movable, or by shifting the stopper in a direction inclined relative to the first surface and the second surface.

In the configuration example of the embodiment described above, the stopper is configured to protrude toward the second surface side. However, the present disclosure is not limited to this example. According to the present disclosure, the stopper may be configured to protrude toward the first surface side, or may be recessed to engage with a protrusion that protrudes from the first surface or the second surface.

In the configuration example of the embodiment described above, the adapter has a substantially circular shape in the plan view. However, the present disclosure is not limited to this example. According to the present disclosure, the shape of the adapter in the plan view is not limited to a substantially circular shape. For example, the adapter may have a rectangular shape in the plan view.

In the configuration example of the embodiment described above, a shift of the operation portion is regulated by contact with the surgical instrument when the surgical instrument is attached to the adapter. However, the present disclosure is not limited to this example. According to the present disclosure, the shift of the operation portion may be regulated by a method other than the use of the surgical instrument when the surgical instrument is attached to the adapter.

In the configuration example of the embodiment described above, the four drive transmission members are provided on the adapter. However, the present disclosure is not limited to this example. According to the present disclosure, the number of the drive transmission members may be any number other than four as long as a plurality of drive transmission members is provided.

In the configuration example of the embodiment described above, the surgical instrument is slid along the second surface of the adapter for attachment and detachment of the surgical instrument. However, the present disclosure is not limited to this example. According to the present disclosure, the surgical instrument may be moved in a direction other than the direction along the second surface of the adapter for attachment and detachment. For example, the surgical instrument may be moved in a direction perpendicular to the second surface of the adapter for attachment and detachment.

In the configuration example of the embodiment described above, the adapter and the drape are separately provided. However, the present disclosure is not limited to this example. According to the present disclosure, the adapter and the drape may be formed integrally with each other.

What is claimed is:

1. An adapter that is detachably provided on a robot arm and transmits a driving force from the robot arm to a surgical instrument, the adapter comprising:
   a base body that includes a first surface including an opening and attached to the robot arm, and a second surface to which the surgical instrument is attached;
   an engaging portion that is configured to be movable between an advanced position corresponding to the opening of the first surface and a retracted position retracted from the advanced position, and engages with the robot arm at the advanced position;
   an urging member that urges the engaging portion in a direction from the retracted position to the advanced position;
   an operation portion connected to the engaging portion to shift the engaging portion to the retracted position while resisting an urging force of the urging member; and
   a stopper that stops the operation portion to prevent a shift of the engaging portion from the retracted position to the advanced position.

2. The adapter according to claim 1, wherein
   the engaging portion is configured to be movable relative to the base body in a predetermined direction parallel to the direction from the retracted position to the advanced position, and
   the stopper is configured to be shifted in a direction orthogonal to the predetermined direction where the engaging portion is movable to switch between a state of stopping the operation portion and a state of releasing the stop of the operation portion.

3. The adapter according to claim 2, wherein the stopper is configured to be moved in a direction where the first surface and the second surface are arranged in the direction orthogonal to the predetermined direction where the engaging portion is movable to switch between the state of stopping the operation portion and the state of releasing the stop of the operation portion.

4. The adapter according to claim 3, wherein the stopper is configured to protrude toward the second surface, and engage with a stopping portion provided on the second surface side of the base body to stop the operation portion.

5. The adapter according to claim 4, wherein
   the base body has a first base member including the first surface, and a second base member including the second surface, and
   the stopping portion is provided at a circumferential portion of the second base member.

6. The adapter according to claim 4, wherein the stopper is configured to shift in such a manner as to release engagement with the stopping portion at the time of attachment to the robot arm.

7. The adapter according to claim 2, wherein the stopper is configured to shift in accordance with bending deformation of a connection portion between the operation portion and the engaging portion to switch between the state of stopping the operation portion and the state of releasing the stop of the operation portion.

8. The adapter according to claim 1, wherein the engaging portion, the operation portion, and the stopper are formed integrally with each other.

9. The adapter according to claim 1, further comprising a regulation portion that is connected to the engaging portion and the operation portion, and contacts the surgical instrument to regulate a shift of the engaging portion when the surgical instrument is attached to the second surface.

10. The adapter according to claim 9, wherein the regulation portion is configured to protrude toward the surgical instrument.

11. The adapter according to claim 9, wherein
the base body includes an opening where the regulation portion is disposed when the engaging portion is shifted to the advanced position, and
the opening has an elongated shape and is formed in an outer circumferential surface of the base body.

12. The adapter according to claim 1, further comprising a drive transmission member that is rotatable on the base body, and transmits a rotation of a drive member provided on the robot arm to a driven portion provided on the surgical instrument.

13. The adapter according to claim 1, wherein the urging member is disposed substantially at a center of the adapter as viewed in a direction where the first surface and the second surface are arranged.

14. The adapter according to claim 1, wherein the adapter is attached to the robot arm via a drape.

15. The adapter according to claim 1, wherein the adapter is provided integrally with a drape that covers the robot arm.

16. A robotic surgical system comprising:
a robot arm including an attachment portion;
a surgical instrument attached to the robot arm; and
an adapter that is attached to the attachment portion of the robot arm, and transmits a driving force from the robot arm to the surgical instrument attached to the adapter,
wherein the adapter includes:
a base body that includes a first surface including an opening and attached to the robot arm, and a second surface to which the surgical instrument is attached;
an engaging portion that is configured to be movable between an advanced position corresponding to the opening of the first surface and a retracted position retracted from the advanced position, and engages with the robot arm at the advanced position;
an urging member that urges the engaging portion in a direction from the retracted position to the advanced position;
an operation portion connected to the engaging portion to shift the engaging portion to the retracted position while resisting an urging force of the urging member; and
a stopper that stops the operation portion to prevent a shift of the engaging portion from the retracted position to the advanced position.

17. The robotic surgical system according to claim 16, wherein the attachment portion of the robot arm includes an engaging protrusion that is inserted into the opening of the adapter and includes a groove with which the engaging portion of the adapter engages.

18. The robotic surgical system according to claim 17, wherein
a plurality of the engaging protrusions is provided, and
a plurality of the openings of the adapter is formed in the first surface substantially at equal intervals.

19. The robotic surgical system according to claim 16, wherein
the attachment portion of the robot arm includes a boss, and
the first surface of the adapter includes a positioning hole into which the boss of the robot arm fits.

20. An adapter attaching method for attaching an adapter to a robot arm by engagement between the robot arm and an engaging portion that is movable between an advanced position corresponding to an opening formed in the adapter and a retracted position retracted from the advanced position, the engagement being made at the advanced position, the adapter attaching method comprising:
shifting the engaging portion to the retracted position while resisting an urging force for urging the engaging portion in a direction from the retracted position to the advanced position by operating an operation portion connected to the engaging portion;
bringing the adapter into contact with the robot arm in a state where the operation portion is stopped by a stopper to prevent a shift of the engaging portion from the retracted position to the advanced position; and
releasing the stop of the operation portion by the stopper to allow engagement between the adapter and the robot arm.

* * * * *